(12) United States Patent
Simanzhenkov et al.

(10) Patent No.: US 11,760,704 B2
(45) Date of Patent: Sep. 19, 2023

(54) OXIDATIVE DEHYDROGENATION COPRODUCTION

(71) Applicant: NOVA Chemicals (International) S.A., Fribourg (CH)

(72) Inventors: Vasily Simanzhenkov, Calgary (CA); Shahin Goodarznia, Calgary (CA)

(73) Assignee: NOVA Chemicals (International) S.A., Fribourg (CH)

( * ) Notice: Subject to any disclaimer, the term of this patent is extended or adjusted under 35 U.S.C. 154(b) by 0 days.

(21) Appl. No.: 17/630,000

(22) PCT Filed: Aug. 17, 2020

(86) PCT No.: PCT/IB2020/057741
§ 371 (c)(1),
(2) Date: Jan. 25, 2022

(87) PCT Pub. No.: WO2021/038374
PCT Pub. Date: Mar. 4, 2021

(65) Prior Publication Data
US 2022/0251004 A1     Aug. 11, 2022

Related U.S. Application Data

(60) Provisional application No. 62/892,810, filed on Aug. 28, 2019.

(51) Int. Cl.
*C07C 5/48* (2006.01)
*C07C 27/12* (2006.01)
(Continued)

(52) U.S. Cl.
CPC .............. *C07C 5/48* (2013.01); *C07C 27/12* (2013.01); *C07C 45/28* (2013.01); *C07C 51/21* (2013.01); *C07C 51/215* (2013.01); *C07C 2523/20* (2013.01); *C07C 2523/22* (2013.01); *C07C 2523/28* (2013.01); *C07C 2523/32* (2013.01);
(Continued)

(58) Field of Classification Search
None
See application file for complete search history.

(56) References Cited

U.S. PATENT DOCUMENTS

2013/0261348 A1* 10/2013 Scates ................... C07C 29/141
                                                            568/881
2016/0023963 A1*  1/2016 Maat .......................... B01J 8/04
                                                            585/329
2019/0135715 A1   5/2019 Simanzhenkov et al.

FOREIGN PATENT DOCUMENTS

EP          0480594        4/1992
WO    WO-2019034435 A1 *  2/2019  ............. C07C 11/04

OTHER PUBLICATIONS

International Preliminary Report on Patentability in International Appln. No. PCT/IB2020/057741, dated Mar. 1, 2022, 7 pages.
(Continued)

*Primary Examiner* — In Suk C Bullock
*Assistant Examiner* — Alyssa L Cepluch
(74) *Attorney, Agent, or Firm* — Fish & Richardson P.C.

(57) ABSTRACT

A system and method for coproduction in the production of ethylene, including contacting ethane with an oxidative dehydrogenation (ODH) catalyst in presence of oxygen in a first reactor to dehydrogenate ethane to ethylene, and contacting a first-reactor effluent with an ODH catalyst in a second reactor to form ethanol and acetaldehyde.

18 Claims, 3 Drawing Sheets

(51) Int. Cl.
*C07C 51/215* (2006.01)
*C07C 45/28* (2006.01)
*C07C 51/21* (2006.01)

(52) U.S. Cl.
CPC .... *C07C 2523/44* (2013.01); *C07C 2523/648* (2013.01)

(56) References Cited

OTHER PUBLICATIONS

International Search Report and Written Opinion in International Appln. No. PCT/IB2020/057741, dated Nov. 27, 2022, 9 pages.

\* cited by examiner

OXIDATIVE DEHYDROGENATION COPRODUCTION

CROSS-REFERENCE TO RELATED APPLICATION

This application is a National Stage Application under 35 U.S.C. 0371 and claims the benefit of International Application No. PCT/IB2020/057741, filed Aug. 17, 2020, which claims priority to U.S. Ser. No. 62/892,810, filed on Aug. 28, 2019. The disclosure of the prior applications is considered part of and is incorporated by reference in the disclosure of this application.

TECHNICAL FIELD

This disclosure relates to coproduction in oxidative dehydrogenation.

BACKGROUND ART

Catalytic oxidative dehydrogenation of alkanes into corresponding alkenes is an alternative to steam cracking. In contrast to steam cracking, oxidative dehydrogenation (ODH) may operate at lower temperature and generally does not produce coke. For ethylene production, ODH can provide a greater selectivity for ethylene than does steam cracking. The ODH may be performed in a reactor vessel having catalyst for the conversion of an alkane to a corresponding alkene. The concept of ODH has been known since at least the late 1960's. Since that time, considerable effort has been expended on improving the ODH process and associated catalyst efficiency and selectivity.

SUMMARY OF INVENTION

Provided in this disclosure is a method of coproduction in the production of ethylene. The method includes contacting ethane with an ODH catalyst in presence of oxygen in a first reactor to dehydrogenate ethane to ethylene and to form at least carbon dioxide and water. The method includes discharging a first-reactor effluent from the first reactor to a second reactor. The first-reactor effluent includes ethylene, carbon dioxide, water, and, optionally, additional components. The method includes contacting the first-reactor effluent with an ODH catalyst in the second reactor to form at least ethanol and acetaldehyde. The method includes discharging a second-reactor effluent from the second reactor. The second-reactor effluent includes ethylene, ethanol, acetaldehyde, and, optionally, additional components.

Further provided in this disclosure is a method of coproduction in a system that converts ethane to ethylene. The method includes feeding ethane, oxygen, and a diluent to a first reactor. The method includes contacting ethane with an ODH catalyst in the first reactor to produce at least ethylene, acetic acid, carbon dioxide, and water. The method includes discharging from the first reactor a first-reactor effluent having at least ethylene, acetic acid, carbon dioxide, and water. The method includes removing oxygen from the first-reactor effluent. The method includes contacting the first-reactor effluent with an ODH catalyst in a second reactor to produce at least ethanol and acetaldehyde. The method includes discharging from the second reactor a second-reactor effluent having at least ethylene, ethanol, acetaldehyde, acetic acid, carbon dioxide, and water.

Further provided in this disclosure is a method of coproduction in the conversion of ethane to ethylene. The method includes contacting ethane with an ODH catalyst in presence of oxygen at a temperature of less than 450° C. in a first ODH reactor to generate ethylene, acetic acid, carbon dioxide, carbon monoxide, and water. The method includes discharging from the first ODH reactor a first-reactor effluent having ethylene, acetic acid, carbon dioxide, carbon monoxide, water, and unreacted ethane through an oxygen-separation vessel to a second ODH reactor. The method includes contacting the first-reactor effluent with an ODH catalyst at a temperature of less than 450° C. in the second ODH reactor to generate at least ethanol and acetaldehyde. The method includes discharging from the second ODH reactor a second-reactor effluent having ethylene, ethanol, acetaldehyde, acetic acid, carbon dioxide, carbon monoxide, and water to a separation column.

Also provided in this disclosure is a system to produce ethylene and coproducts. The system includes a first reactor having a first ODH catalyst to dehydrogenate ethane into ethylene and form at least carbon dioxide, carbon monoxide, and water. The system includes a second reactor having a second ODH catalyst to form at least ethanol and acetaldehyde from a first-reactor effluent. The first reactor effluent includes at least ethylene, unreacted ethane, carbon dioxide, carbon monoxide, and water from the first reactor. The second reactor discharges a second-reactor effluent having at least ethylene, ethanol, and acetaldehyde as coproducts.

Further provided in this disclosure is a system to produce ethylene and coproducts. The system includes a first ODH reactor to receive at least ethane and oxygen. The first ODH reactor has a first ODH catalyst to convert ethane into ethylene, generate at least carbon dioxide and water, and convert ethylene into acetic acid. The system includes an oxygen-separation vessel to receive a first-reactor effluent from the first ODH reactor and remove oxygen from the first-reactor effluent. The system includes a second ODH reactor to receive the first-reactor effluent from the oxygen-separation vessel. The second reactor has a second ODH catalyst to generate at least ethanol and acetaldehyde from the first-reactor effluent at an operating temperature of less than 450° C. and discharge a second-reactor effluent having ethylene, ethanol, acetaldehyde, and acetic acid as coproducts.

The details of one or more implementations are set forth in the accompanying drawings and the description below. Other features and advantages will be apparent from the description and drawings, and from the claims.

DESCRIPTION OF EMBODIMENTS

Embodiments of the present techniques are directed to product diversification in the oxidative dehydrogenation (ODH) of ethane to ethylene to generate coproducts, such as ethanol and acetaldehyde, in addition to the product ethylene. Some aspects are directed to low-temperature reactions (e.g., below 450° C.) that produce ethylene from ethane and that may generate byproducts, such as carbon monoxide (CO), carbon dioxide ($CO_2$), and acetic acid. Low-temperature ODH catalysts may be utilized.

In embodiments, at least two ODH reactors in series are employed. Additional ODH reactors may be included in parallel. In some embodiments, a second ODH reactor operates in series downstream of a first ODH reactor. In certain implementations, the two reactors in series may have the same or similar type of ODH catalyst.

For implementations of two reactors (each having ODH catalyst) in series, the first reactor may produce ethylene and the second reactor may convert some of the ethylene produced in the first reactor to ethanol and acetaldehyde as coproducts of the ethylene. Production of these coproducts may enhance profitability of the ODH reactor system that produces ethylene. The balance of ethylene production, ethanol production, and acetaldehyde production (and other coproduct production) by the ODH reactor system may be adjusted depending on market need. Other coproducts may include, for example, acetic acid that is as a byproduct in the ODH conversion of ethane to ethylene in the first reactor. Acetic acid may be produced from ethylene in the first reactor. Acetic acid may also be produced in the second reactor.

Figure 1:
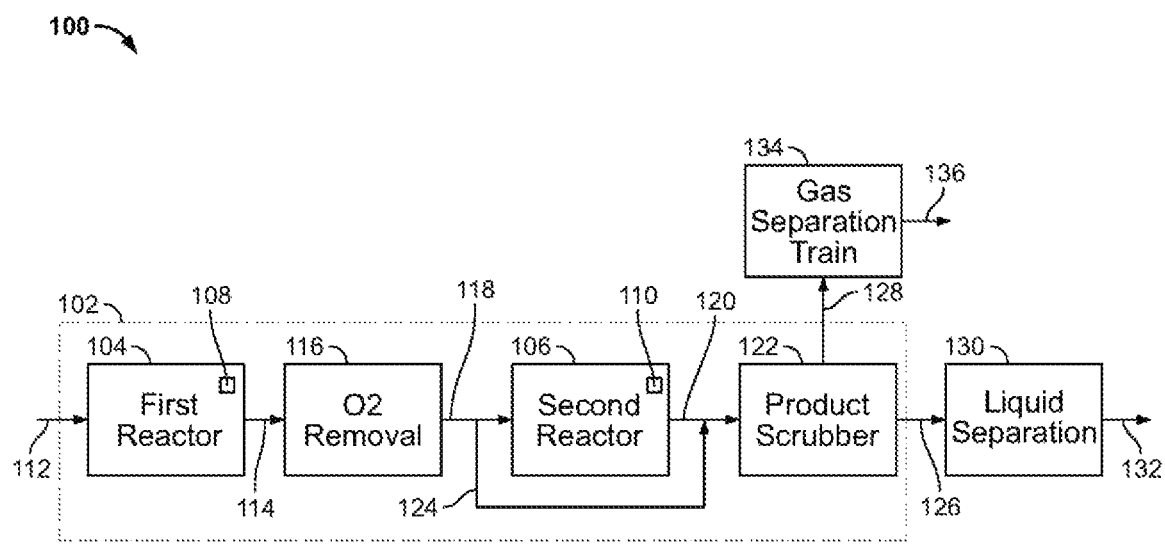
FIG. 1 is a block diagram of oxidative dehydrogenation (ODH) coproduction system including an ODH reactor system having two ODH reactors in series.

The block flow diagram of the ODH system depicted in FIG. 1 is an embodiment of the present techniques. As indicated by FIG. 1, a product effluent stream from a first reactor (having ODH catalyst) can be sent to a second reactor (having ODH catalyst) to convert carbonaceous material (e.g., ethylene) from the first reactor into ethanol and acetaldehyde in the second reactor.

For example, in the second reactor, ethanol may be formed by ethylene hydration: [1] $C_2H_4+H_2O \rightarrow C_2H_6O$ as a bulked chemical reaction. Acetaldehyde may be formed in the second reactor by ethanol oxidative dehydrogenation in presence of $CO_2$ as a mild oxidant: [2] $C_2H_6O+CO_2 \rightarrow O_2H_4O+H_2O+CO$ as a bulked chemical reaction. In certain implementations, the amount of production of ethanol (e.g., via reaction [1]) and acetaldehyde (e.g., via reaction [2]) versus the amount of ethylene production may be adjusted depending, for example, on market need and other factors. Moreover, it may be beneficial that oxygen ($O_2$) not be present in second reactor to avoid oxidation of ethanol and acetaldehyde to acetic acid in the second reactor. Lastly, the residence time in the second reactor to generate ethanol via the aforementioned reaction [1] (ethylene hydration) and acetaldehyde via the aforementioned reaction [2] (ethanol oxidative dehydrogenation) may be similar or at least within an order of magnitude of the residence time to generate ethylene from ethane via the ODH reaction in the first reactor.

FIG. 1 is an ODH coproduction system 100 having an ODH reactor system 102 with a first ODH reactor 104 and a second ODH reactor 106 in series. The reactors 104, 106 are labeled as "ODH" reactors because the reactors 104, 106 have ODH catalyst and because ODH reactions may occur in the reactors 104, 106. Reactions other than ODH may also occur in the reactors 104, 106. The "oxidative dehydrogenation" or "ODH" reaction may refer to the combination of endothermic dehydration of an alkane and exothermic oxidation of hydrogen.

In some cases, the two ODH reactors 104, 106 in series may operate at similar operating conditions of temperature and pressure. However, in other instances, the operating temperature in the first ODH reactor 104 is different than the operating temperature in the second ODH reactor 106. The operating pressure in the second ODH reactor 106 may be less than the operating pressure in the first ODH reactor 104 to facilitate flow of effluent from the first ODH reactor to the second ODH reactor.

The first ODH reactor 104 and the second ODH reactor 106 may each be a fixed-bed reactor (e.g., a tubular fixed-bed reactor), fluidized-bed reactor, ebullated bed reactor, or heat-exchanger type reactor, and so on. The reactors or reactor system generally utilize a heat-transfer fluid for removing heat from the reactor for temperature control of the reactor. The heat transfer (cooling) medium can be, for example, oil or molten salt.

For a fixed-bed reactor, reactants may be introduced into the reactor at one end and flow past an immobilized catalyst. Products are formed and an effluent having the products may discharge at the other end of the reactor. The fixed-bed reactor may have one or more tubes (e.g., ceramic tubes) each having a bed of catalyst and for flow of reactants (e.g., ethane in first reactor 104, ethylene in second reactor 106) and products (e.g., ethylene in first reactor 104, ethanol and acetaldehyde in second reactor 106). The tubes may include, for example, a steel mesh. Moreover, a heat-transfer (e.g., cooling) jacket adjacent the tube(s) may provide for temperature control of the reactor. The aforementioned heat transfer fluid may flow through the reactor jacket.

In other embodiments, the first ODH reactor 104 and the second ODH reactor 106 are each a fluidized bed reactor. In implementations, a fluidized bed reactor may have a support for the ODH catalyst. The support may be a porous structure or distributor plate and disposed in a bottom portion of the reactor. Reactants may flow upward through the support at a velocity to fluidize the bed of ODH catalyst (e.g., the catalyst rises and begins to swirl around in a fluidized manner). The reactants are converted to products upon contact with the fluidized catalyst. An effluent having products may discharge from an upper portion of the reactor. The fluidized bed reactor may have a heat-transfer (e.g., cooling) tubers or jacket to facilitate temperature control of the reactor. The aforementioned heat transfer fluid may flow through the reactor tubers or jacket. Lastly, the fluidized bed reactor can be (1) a non-circulating fluidized bed, (2) a circulating fluidized bed with regenerator, or (3) a circulating fluidized bed without regenerator.

As indicated, the first reactor 104 has an ODH catalyst 108 and the second reactor 106 also has an ODH catalyst 110. The ODH catalyst 110 in the second reactor 106 may be the same catalyst type as the ODH catalyst 108 in the first reactor 104. In some implementations, the catalyst 108, 110 is a low temperature catalyst that includes molybdenum, vanadium, tellurium, niobium, and oxygen wherein the molar ratio of molybdenum to vanadium is from 1:0.12 to 1:0.49, the molar ratio of molybdenum to tellurium is from 1:0.01 to 1:0.30, the molar ratio of molybdenum to niobium is from 1:0.01 to 1:0.30, and oxygen is present at least in an amount to satisfy the valency of any present metal oxides. The molar ratios of molybdenum, vanadium, tellurium, niobium can be determined by inductively coupled plasma mass spectrometry (ICP-MS). The catalyst may be low temperature in providing for an ODH reaction at less than 450° C., less than 425° C., or less than 400° C.

The catalyst 108, 110 may be a low-temperature ODH catalyst available from NOVA Chemicals Corporation having headquarters in Calgary, Canada. In particular, this implementation of catalyst is a mixed metal oxide having the formula $Mo_aV_bTe_cNb_dPd_eO_f$, where a, b, c, d, e, and f subscripts are relative atomic amounts of the elements Mo, V, Te, Nb, Pd, O, respectively. When a=1, then b=0.01 to 1.0, c=0.01 to 1.0, d=0.01 to 1.0, $0.00 \leq e \leq 0.10$, and f is a number to satisfy the valence state of the catalyst. This catalyst may provide for the ODH reaction to occur at a temperature of less than 400° C. or less than 450° C. Also, the ODH catalyst 108, 110 may be, for example, a fixed bed or in a fluidized bed.

In operation, the first ODH reactor 104 receives a feed 112 that may be one or more streams. The feed 112 may include ethane, oxygen, diluent, and so forth. The diluent may be, for example, carbon dioxide or nitrogen. Other diluents are applicable.

The first reactor 104 converts ethane to ethylene in an ODH reaction via the ODH catalyst 108. Byproducts may include water, carbon monoxide (CO), and carbon dioxide ($CO_2$). A byproduct may be acetic acid ($C_4H_4O_2$) formed by the conversion of ethane or ethylene to acetic acid. For example, ethylene may be oxidized to acetic acid as in the bulked chemical reaction $C_2H_4+O_2 \rightarrow C_4H_4O_2$. This bulked chemical reaction may involve $C_2H_4+H_2O \rightarrow C_2H_5OH$ followed by $C_2H_5OH+O_2 \rightarrow C_4H_4O_2+H_2O$. The byproduct acetic acid formed in the first reactor 104 may be a coproduct.

The effluent 114 from the first ODH reactor 104 may include ethylene, CO, $CO_2$, water, acetic acid, and unreacted ethane. The effluent 114 may be labeled as a product effluent of the first reactor 104 because the effluent 114 has products, such as ethylene and acetic acid, from the first reactor 104. The effluent 114 may be processed to remove oxygen ($O_2$) from the effluent 114 prior to introduction of the effluent 114 to the second ODH reactor 106. A reason to remove $O_2$ may be to promote the production of ethanol and acetaldehyde in the second ODH reactor 106. In particular, the removal of $O_2$ from the effluent 114 may beneficially deprive the second ODH reactor 106 of $O_2$ and thus avoid oxidation of ethanol (and acetaldehyde) via $O_2$ into acetic acid in the second reactor 106.

The oxidative dehydrogenation of ethanol to acetic acid using $O_2$ (e.g., $C_2H_6O+O_2 \rightarrow O_2H_4O+H_2O$) (as in the first reactor 104) may have faster kinetics compared to selective oxidation of ethanol and acetaldehyde to acetic acid using $CO_2$ (e.g., $O_2H_4O+CO_2 \rightarrow C_2H_4O_2+CO$) (as in the second reactor 106). $O_2$ is generally a stronger oxidizer than $CO_2$. Therefore, when $O_2$ is present in the reactor, the $O_2$ may oxidize all (or most of) the ethanol and acetaldehyde to acetic acid. Thus, the presence of $O_2$ may hinder sustained formation of ethanol and acetaldehyde (intermediate between acetic acid and ethanol) by consuming (oxidizing) most of ethanol and acetaldehyde to acetic acid. There is less probability to produce and discharge ethanol and acetaldehyde from the second reactor 106 if $O_2$ is present in the second reactor 106.

Therefore, the ODH reactor system 102 includes an $O_2$ removal system 116 that receives the effluent 114 from the first ODH reactor 104. One implementation of an $O_2$ removal system 116 is to remove $O_2$ by reacting $O_2$ in the effluent 114 with CO in the effluent 114 to form additional $CO_2$ than entering in the effluent 114. The $O_2$ removal system may include a vessel or reactor having a selective oxidation catalyst that provides for the reaction of CO with $O_2$ to give $CO_2$. The selective oxidation catalyst may be, for example, a silver-cerium (IV) oxide silica ($Ag-CeO_2/SiO_2$). Other implementations of an $O_2$ removal system (e.g., a vessel having a separation membrane, etc.) are applicable.

The $O_2$ removal system 116 may discharge a processed effluent 118 that is the first-reactor effluent 114 without the $O_2$ removed by the $O_2$ removal system 116. The processed effluent 118 may include ethylene, CO, $CO_2$, water, acetic acid, and unreacted ethane. The processed effluent 118 may be sent to the second ODH reactor 106. At least two reactions may occur in second ODH reactor 106: (a) hydration of ethylene to ethanol as in [1] $C_2H_4+H_2O \rightarrow C_2H_6O$; and (b) oxidative dehydrogenation of ethanol to acetaldehyde as in [2] $C_2H_6O+CO_2 \rightarrow C_2H_4O+H_2O+CO$. An example of a third reaction may be the oxidation of acetaldehyde to acetic acid as in [3] $C_2H_4O+CO_2 \rightarrow C_2H_4O_2+CO$.

The effluent 120 from the second ODH reactor 106 may include ethane, ethylene, CO, $CO_2$, water, acetic acid, ethanol, and acetaldehyde. The effluent 120 may be labeled as a product effluent of the second reactor 106 because the effluent 120 has products from the second reactor 106. The products in the effluent 120 discharged from the second reactor 106 may include ethylene, acetic acid, ethanol, or acetaldehyde, or any combination thereof, and additional products.

The effluent 120 from the second ODH reactor 106 may be fed to a liquid product scrubber 122. Some of the processed effluent 118 from the $O_2$ removal system 116 may bypass 124 the second ODH reactor 106 (e.g., through a bypass 124 conduit) and sent to the product scrubber 122. The percent of the processed first-reactor effluent 118 sent directly to the scrubber 122 (bypassing the second reactor 106) may range from 0 to 100.

As discussed, the second ODH reactor 106 may convert a portion of the ethylene to ethanol, acetaldehyde, and acetic acid. The ethanol, acetaldehyde, and acetic acid may be referred to as oxygenated products. The split ratio of the processed first-reactor effluent 118 going to the second ODH reactor 106 versus going directly to the liquid product scrubber 122 may be adjusted depending, for example, on the desired selectivity towards the oxygenated product versus the desired selectivity towards ethylene. Such may be influenced by market need or other considerations.

The liquid product scrubber 122 may be a vessel (e.g., column, tower, etc.) to separate liquid products from gas products. The liquid product scrubber 122 may be a separation vessel, such as a quench tower, a spray tower, a venture scrubber, or a packed tower, and the like. In certain implementations with the scrubber 122 as a packed tower, water may be fed to the top portion of tower vessel as a shower internal to the tower to scrub off the liquid product mixture in the packed tower. The water can be, for example, demineralized water, process water, water having other components such as acetic acid, and water of varying quality.

A packed tower (a packed-bed column) may be a vessel (chamber) having a bed of packing. The packing or packing material may be various shapes, such as Raschig rings, spiral rings, or Berl saddles, and provide surface area for liquid-gas contact. The packing may be held in place, for example, by wire mesh retainers and supported by in a bottom portion of the packed-bed scrubber. In operation, scrubbing liquid may be introduced above the packing and flows down through the packing bed. In vertical designs (packed towers), a gas stream may flow up the chamber (countercurrent to the liquid).

A spray tower (or spray chamber) may be a cylindrical vessel made of steel or plastic and having nozzles that provide for spraying liquid into the vessel. The flow of inlet gas and inlet liquid may be in the opposite direction (countercurrent flow). In certain implementations, several nozzles may be place along the spray tower at different heights for the introduction of liquid spray.

A liquid product discharge 126 from the scrubber 122 may include ethanol, acetaldehyde, acetic acid, and water. A gas product discharge 128 from the scrubber 122 may include ethylene, CO, $CO_2$, and ethane. In some implementations, the liquid product discharge 126 is from a bottom portion of the scrubber 122, and the gas product discharge 128 is from an upper portion of the scrubber 122.

The liquid product discharge 126 may be processed in a liquid-product separation system 130 that separates liquid coproducts. The separation system 130 may include one or more distillation columns, liquid-to-liquid extraction columns, and the like, to separate the liquid products. The arrow 132 represents multiple discrete product streams from the separation system 130. The multiple separate product streams may include (1) an ethanol stream, (2) an acetaldehyde stream, and (3) an acetic acid stream. These streams may be labeled as coproducts of the ethylene production in the ODH reactor system 102.

As mentioned, gas product discharge 128 from the liquid product scrubber 122 may include ethylene, CO, $CO_2$, and ethane. The gas product discharge 128 from the scrubber 122 may be sent to a gas-product separation train 134. The separation train 134 may include, for example, multiple columns (e.g., distillation column(s), extraction columns, scrubber columns, etc.). Two or more of the columns may be disposed in series to form a train of columns. In some examples, the separation train 134 is a series of at least three distillation columns.

The arrow 136 represents multiple discrete streams that discharge from the separation train 134. The multiple separate streams may include (1) an ethane stream, (2) an ethylene stream, (3) a CO stream, and (4) a $CO_2$ stream. In certain implementations, the ethane stream may be recycled as feed to the first ODH reactor 104, the ethylene stream is product that can be subjected to additional processing or consumed, and the $CO_2$ may be sent to a $CO_2$ capture or conversion plant (unit), and the like.

Figure 2:
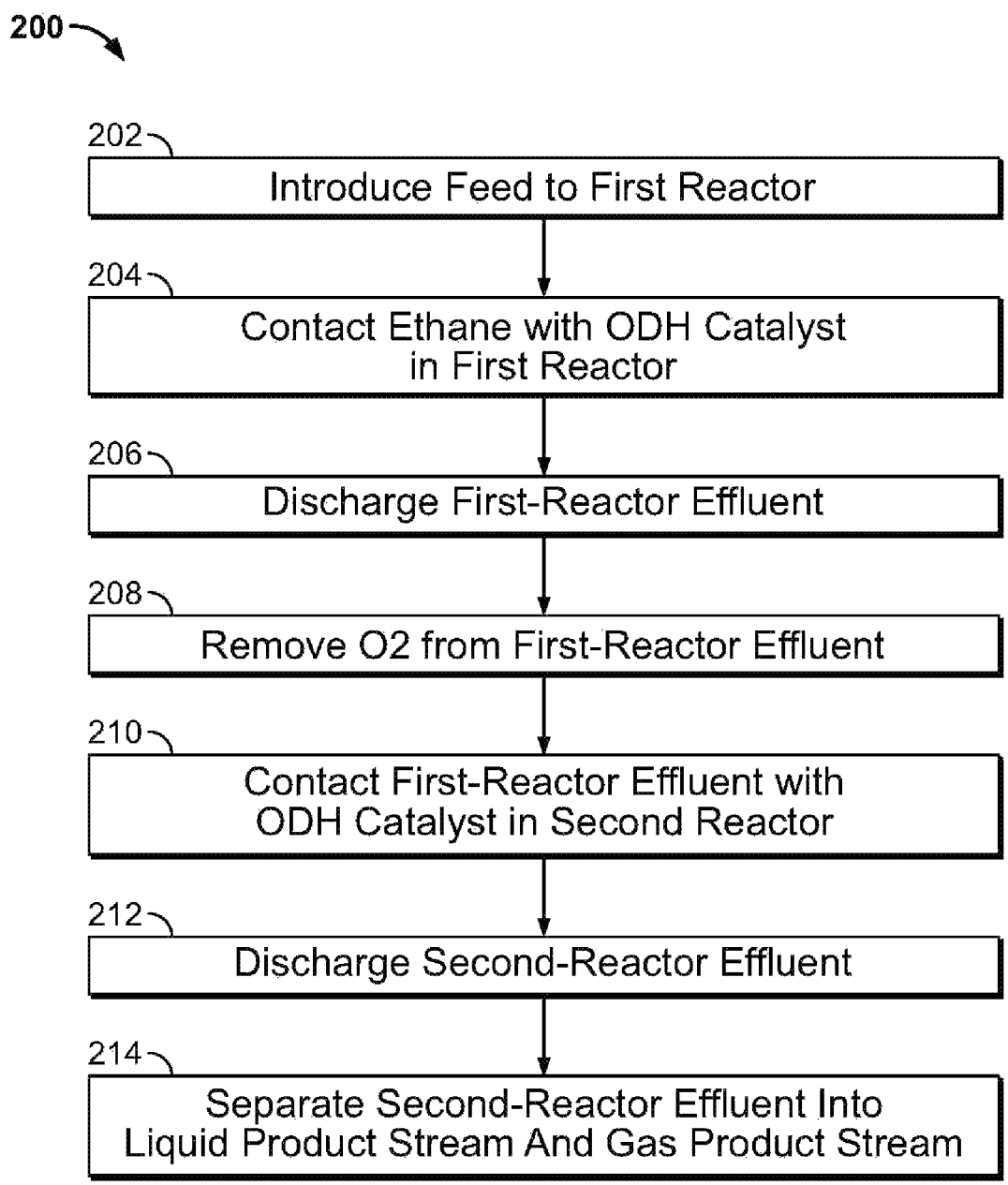
FIG. 2 is a block flow diagram of a method of coproduction in an ODH system that converts ethane to ethylene.

FIG. 2 is a method 200 of coproduction in an ODH system that converts ethane to ethylene. The method involves at least two reactors in series. Each reactor has an ODH catalyst. The two reactors may each be a fixed-bed reactor. A fixed-bed reactor may have a cylindrical tube(s) filled with catalyst pellets as a bed of catalyst. In operation, reactants flow through the bed and are converted into products. The catalyst in the reactor may be one large bed, several horizontal beds, several parallel packed tubes, or multiple beds in their own shells, and so on.

In other implementations, the two reactors may each be a fluidized bed reactor. A fluidized bed reactor may be a vessel in which a fluid is passed through a solid granular catalyst (e.g., shaped as spheres or particles) at adequate velocity to suspend the solid catalyst and cause the solid catalyst to behave as though a fluid. In some implementations, the first reactor as a fluidized bed reactor has a recirculating mode of operation in circulation between reactor and regenerator of the fluidized bed reactor-regenerator system. In contrast for some implementations, the second reactor may generally not employ such recirculation, as the recirculation may promote excessive production of acetic acid. If the second fluidized-bed reactor is equipped with recirculation, the recirculation valves may be fully closed in certain instances to be operational as the second reactor for producing a desired balance of coproducts.

At block 202, the method includes feeding ethane, oxygen, and a diluent to the first reactor having ODH catalyst. The feed may be provided through one or more conduits. The oxygen may be introduced into the first reactor separate from the ethane. The oxygen may be fed to the reactor by feeding air to the reactor. The diluent may be, for example, carbon dioxide or nitrogen.

At block 204, the method includes contacting ethane with the ODH catalyst in presence of oxygen in the first reactor to dehydrogenate ethane to ethylene and to form carbon dioxide, carbon monoxide, water, and acetic acid. The acetic acid can be characterized as a byproduct and labeled as a coproduct of the produced ethylene.

At block 206, the method includes discharging a first-reactor effluent (a product effluent of the first reactor) from the first reactor to the second reactor or to a packed column (as described with respect to block 214). A portion of the first-reactor effluent may be sent to the second reactor and the remaining portion of the first-reactor effluent may be sent to the packed column. The first-reactor effluent may be sent to the packed column to avoid conversion of ethylene in the first-reactor effluent to coproducts in the second reactor.

The first-reactor effluent includes ethylene, carbon dioxide, carbon monoxide, water, acetic acid, and unreacted ethane. The first-reactor effluent may be processed in route to the second reactor or to the packed column. For instance, the method may remove oxygen from the first-reactor effluent, as discussed below with respect to block 208. The first-reactor effluent may discharge through an oxygen separation vessel (see block 208) to the second reactor or to the packed column.

At block 208, the method includes removing oxygen from the first-reactor effluent. In this embodiment, the method includes removing oxygen from the first-reactor effluent upstream of the second reactor and the packed column. Thus, the first-reactor effluent fed to the second reactor (and to the packed column) may be processed first-reactor effluent having oxygen removed.

In implementations, the removal of oxygen from the first-reactor effluent may involve flowing the first-reactor effluent through an oxygen-separation vessel. In some examples, the oxygen is removed via a selective oxidation catalyst in the oxygen-separation vessel as an oxygen-separation reactor. For instance, the removal of oxygen may be by consuming oxygen in the reaction of oxygen with carbon monoxide present to give carbon dioxide. The selective oxidation catalyst may be, for example, a silver-cerium (IV) oxide silica ($Ag-CeO_2/SiO_2$) or a copper/zinc/zirconium oxide ($CuZnZrO_x$), and the like. Other implementations of an $O_2$ removal system (e.g., a vessel having a separation membrane, etc.) are applicable.

As mentioned, some or all of the processed first-reactor effluent (having $O_2$ removed) may discharge from the $O_2$ removal system to the packed column and thus bypass the second reactor. The percent of the processed first-reactor effluent sent to the packed tower (bypassing the second reactor) may be modulated and range from 0 to 100.

At block 210, the method includes contacting the processed first-reactor effluent with the ODH catalyst in the second reactor to form ethanol and acetaldehyde. In some instances, the method may include adding carbon dioxide to the second reactor to favor production of acetaldehyde over production of ethanol in the second reactor. Additional acetic acid may also be formed. The ethanol and acetaldehyde (and acetic acid) may be coproducts along with the ethylene produced in the first reactor.

Without $O_2$ in the second reactor, there may be no measurable conversion of ethane to ethylene in the second reactor. A trace conversion of ethane to ethylene may occur in the second reactor, for example, due to any oxygen present on the catalyst surface.

The reaction kinetics in the second reactor may favor production of acetaldehyde over acetic acid or may favor production of acetic acid over acetaldehyde, depending on the reaction conditions. Reaction conditions that may be adjusted included temperature, pressure, GHSV, feed composition, and the like.

In the Example discussed below, more acetic acid was produced than acetaldehyde in the laboratory ODH reactor performing as a second reactor in a series of two ODH reactors.

As discussed, reactions that may occur in the second reactor include: [1] $C_2H_4+H_2O \rightarrow C_2H_6O$ (ethanol); [2] $C_2H_6O+CO_2 \rightarrow C_2H_4O$ (acetaldehyde)$+H_2O+CO$; and [3] $C_2H_4O+CO_2 \rightarrow C_2H_4O_2$ (acetic acid)$+CO$. In certain implementations, $CO_2$ may be added to the second reactor to favor production of acetaldehyde over production of ethanol in the second reactor. Conversely, in some implementations, some $CO_2$ is removed from the first-reactor effluent to favor production of ethanol over acetaldehyde in the second reactor.

The addition of more $CO_2$ (e.g., increasing concentration of $CO_2$ in the first-reactor effluent feed) may increase the rate of formation of acetaldehyde and acetic acid in the second reactor. The sensitivity of the (1) reaction of ethanol/$CO_2$ to acetaldehyde and (2) reaction of acetaldehyde/$CO_2$ to acetic acid in relation to change in feed $CO_2$ concentration may depend on reaction conditions. In one example, the ODH reactor system includes a conduit to add $CO_2$ to the effluent from the first reactor flowing to the second reactor. In another example, a conduit is utilized to add $CO_2$ directly to the second reactor. However, in other examples, no $CO_2$ is added to either the first-reactor effluent or to the second reactor but instead the amount of $CO_2$ fed to the second reactor is the amount of $CO_2$ that discharges in the first-reactor effluent from the first reactor.

As for removal of $CO_2$ from the first-reactor effluent, reactions conditions in the second reactor may determine if less $CO_2$ in the feed to the second reactor would hinder formation of acetaldehyde (and acetic acid) in the second reactor. A $CO_2$ removal unit (if employed) may be disposed between the first reactor and the second reactor to remove $CO_2$ from the first-reactor effluent flowing to the second reactor. The $CO_2$ removal unit may be, for example, an amine tower or caustic tower. In implementations, liquid in the first-reactor effluent may be removed before subjecting the first-reactor effluent to the $CO_2$ removal unit.

At block 212, the method include discharging a second-reactor effluent (a product effluent of the second reactor) from the second reactor. For example, the second-reactor effluent may be discharged to a separation column, such as a column having packing to separate liquid from gas. The second-reactor effluent includes ethylene, ethanol, and acetaldehyde as coproducts. The second-reactor effluent may also typically include acetic acid as a coproduct. Further, the second-reactor effluent may include carbon dioxide, carbon monoxide, water, unreacted ethane, and so on.

At block 214 the method includes separating the second-reactor effluent into a liquid stream and a gas stream. The liquid stream may include ethanol, acetaldehyde, acetic acid, and water. The gas stream may include ethylene, ethane, carbon dioxide, and carbon monoxide. In implementations, the separating may involve separating the second-reactor effluent into the gas stream and the liquid stream in a packed column, discharging the gas stream overhead from the packed column, and discharging the liquid stream from a bottom portion of the packed column. The packed column may be labeled, for example, as a scrubber or liquid scrubber. The packed column may be the packed-tower embodiment of the liquid product scrubber 122 depicted in FIG. 1.

The method may include maintaining an operating temperature of the first reactor and an operating temperature of the second reactor at less than 450° C., less than 425° C., or less than 400° C. As for operating pressure, the reactor inlet pressure for each reactor may be less than 80 pound per square inch gauge (psig), or less than 70 psig. The reactor inlet pressure for each reactor may in the range of 1 psig to 80 psig, or in the range of 5 psig to 75 psig. Other operating conditions of the reactor in the embodiment of the reactor as a tubular fixed-bed reactor may be gas hourly space velocity (GHSV) in the range of 200 hour$^{-1}$ to 10,000 hour$^{-1}$ and a linear velocity range of the feed through the reactor of at least 5 cubic centimeters per second (cm$^3$/sec). The ODH catalyst in the first reactor and the ODH catalyst in the second reactor may each be a mixed metal oxide having formula $Mo_aV_bTe_cNb_dPd_eO_f$, where a, b, c, d, e, and f subscripts are relative atomic amounts of elements Mo, V, Te, Nb, Pd, O, respectively, and when a=1, b=0.01 to 1.0, c=0.01 to 1.0, d=0.01 to 1.0, 0.00≤e≤0.10, and f is a number to satisfy valence state of the catalyst.

An embodiment is a method of coproduction in the production of ethylene. The method includes contacting ethane with an ODH catalyst in presence of oxygen in a first reactor to dehydrogenate ethane to ethylene and to form carbon dioxide and water. The contacting of the ethane with the ODH catalyst in the presence of oxygen in the first reactor may also form carbon monoxide and acetic acid. The method includes discharging a first-reactor effluent from the first reactor to a second reactor. The first-reactor effluent includes ethylene, carbon dioxide, and water. The first-reactor effluent may also include carbon monoxide, acetic acid, and unreacted ethane. The method may include removing oxygen from the first-reactor effluent upstream of the second reactor. The first-reactor effluent is contacted with an ODH catalyst in the second reactor to form ethanol and acetaldehyde. A second-reactor effluent is discharged from the second reactor. The second-reactor effluent includes ethylene, ethanol, and acetaldehyde. The ethylene, ethanol, and acetaldehyde may be coproducts. The second-reactor effluent may also include carbon dioxide, carbon monoxide, water, and acetic acid. Acetic acid may be a coproduct. The method may include maintaining an operating temperature of the first reactor and an operating temperature of the second reactor at less than 450° C. The method may include adding carbon dioxide to the second reactor to favor production of acetaldehyde over production of ethanol.

The method may include separating the second-reactor effluent into a liquid stream and a gas stream, wherein the liquid stream includes ethanol, acetaldehyde, acetic acid, and water, and wherein the gas stream includes ethylene, ethane, carbon dioxide, and carbon monoxide. The separating may involve separating the second-reactor effluent into the gas stream and the liquid stream in a packed column, discharging the gas stream overhead from the packed column, and discharging the liquid stream from a bottom portion of the packed column. Lastly, the ODH catalyst in the first reactor and the ODH catalyst in the second reactor may each be a mixed metal oxide having formula $Mo_aV_bTe_cNb_dPd_eO_f$, where a, b, c, d, e, and f subscripts are relative atomic amounts of elements Mo, V, Te, Nb, Pd, O, respectively, and when a=1, b=0.01 to 1.0, c=0.01 to 1.0, d=0.01 to 1.0, 0.00≤e≤0.10, and f is a number to satisfy the valence state of the catalyst. The variable f may be a number to satisfy at least the valence state of the corresponding elements in the catalyst.

Another embodiment is a method of coproduction in a system that converts ethane to ethylene. The method includes: feeding ethane, oxygen, and a diluent to a first reactor; contacting ethane with an ODH catalyst in the first reactor to produce ethylene, acetic acid, carbon dioxide, and water; discharging from the first reactor a first-reactor effluent having ethylene, acetic acid, carbon dioxide, and water; removing oxygen from the first-reactor effluent; contacting the first-reactor effluent with an ODH catalyst in a second reactor to produce ethanol and acetaldehyde; and discharging from the second reactor a second-reactor effluent having ethylene, ethanol, acetaldehyde, acetic acid, carbon dioxide, and water. The contacting of the ethane with the ODH catalyst in the first reactor may produce carbon monoxide and, therefore, the first-reactor effluent may have carbon monoxide. The second-reactor effluent may also have carbon monoxide. The contacting of the first-reactor effluent with the ODH catalyst in the second reactor may produce acetic acid. An operating temperature of the first reactor and an operating temperature of the second reactor are less than 450° C. In certain implementations, the first reactor and the second reactor each are a fixed-bed reactor having the ODH catalyst in a fixed bed.

Yet another embodiment is a method of coproduction in the conversion of ethane to ethylene. The method includes contacting ethane with an ODH catalyst in presence of oxygen at a temperature of less than 450° C. in a first ODH reactor to generate ethylene, acetic acid, carbon dioxide, and water. The method includes discharging from the first ODH reactor a first-reactor effluent having ethylene, acetic acid, carbon dioxide, water, and unreacted ethane through an oxygen-separation vessel to a second ODH reactor. The method may include removing oxygen from the first-reactor effluent flowing through the oxygen-separation vessel via a selective oxidation catalyst in the oxygen-separation vessel. The method includes contacting the first-reactor effluent with an ODH catalyst at a temperature of less than 450° C. in the second ODH reactor to generate ethanol and acetaldehyde. The method includes discharging from the second ODH reactor a second-reactor effluent having ethylene, ethanol, acetaldehyde, acetic acid, carbon dioxide, and water to a separation column. Ethylene, ethanol, acetaldehyde, and acetic acid in the second-reactor effluent may be coproducts. The first ODH reactor and the second ODH reactor may each be a fluidized bed reactor having the first ODH catalyst and the second ODH catalyst, respectively, in operation as a fluidized bed of catalyst. In other implementations, the first ODH reactor and the second ODH reactor are each a tubular fixed-bed reactor.

Yet another embodiment is a system to produce ethylene and coproducts. The system has a first reactor with a first ODH catalyst to dehydrogenate ethane into ethylene and form carbon dioxide, carbon monoxide, and water. The first reactor may be a fixed-bed reactor having the first ODH catalyst as a fixed bed of catalyst. The first reactor may have a cooling jacket to maintain an operating temperature of the first reactor less than 450° C. A first-reactor effluent from the first reactor includes ethylene, unreacted ethane, carbon dioxide, carbon monoxide, and water. The first reactor may also form acetic acid and, therefore, the first-reactor effluent may include acetic acid. The first reactor may form acetic acid by oxidation of ethylene and ethanol in presence of oxygen. The system includes a second reactor having a second ODH catalyst to form ethanol and acetaldehyde from the first-reactor effluent. An oxygen-separation vessel may be operationally disposed between the first reactor and the second reactor to remove oxygen from the first-reactor effluent. In some implementations, the oxygen-separation vessel may have a selective oxidation catalyst to facilitate removal of oxygen from the first-reactor effluent. The second reactor may be a fixed-bed reactor having the second ODH catalyst as a fixed bed of catalyst. The second reactor may have a heat-transfer (e.g., cooling) jacket to maintain an operating temperature of the second reactor less than 450° C. The second reactor discharges a second-reactor effluent having ethylene, ethanol, and acetaldehyde as coproducts. The second reactor may form acetic acid from the first-reactor effluent. The second reactor may form acetic acid by oxidation of ethanol and acetaldehyde in presence of carbon dioxide. The second-reactor effluent may include acetic acid, carbon dioxide, water, and carbon monoxide. Acetic acid may be a coproduct.

The system may include a separation column to separate the second-reactor effluent into a gas stream and a liquid stream, wherein the gas stream includes ethylene, ethane, carbon monoxide, and carbon dioxide, and wherein the liquid stream includes ethanol, acetaldehyde, acetic acid, and water. In certain implementations, the separation column includes: packing to separate the second-reactor effluent into the gas stream and the liquid stream; an overhead outlet on an upper portion of the separation column to discharge the gas stream; and a bottoms outlet on a lower portion of the separation column to discharge the liquid stream. Lastly, the first ODH catalyst and the second ODH catalyst may each include a mixed metal oxide having formula $Mo_aV_bTe_cNb_dPd_eO_f$, where a, b, c, d, e, and f subscripts are relative atomic amounts of elements Mo, V, Te, Nb, Pd, 0, respectively, and when a=1, b=0.01 to 1.0, c=0.01 to 1.0, d=0.01 to 1.0, 0.00≤e≤0.10, and f is a number to satisfy valence state of the catalyst.

Yet another embodiment is a system to produce ethylene and coproducts. The system includes a first ODH reactor (e.g., a tubular fixed-bed reactor, a fluidized bed reactor, etc.) to receive ethane and oxygen. The first ODH reactor may also receive hydrogen. In some instances, the first ODH reactor receives diluent, such as nitrogen or carbon dioxide, or other diluent. The first ODH reactor has a first ODH catalyst to convert ethane into ethylene, generate carbon dioxide and water, and convert ethylene into acetic acid. The first ODH reactor may also form carbon monoxide. The system includes an oxygen-separation vessel to receive a first-reactor effluent from the first ODH reactor and remove oxygen from the first-reactor effluent. The system includes a second ODH reactor (e.g., a tubular fixed-bed reactor, a fluidized bed reactor, ebullated bed reactor, etc.) to receive the first-reactor effluent from the oxygen-separation vessel. The second reactor has a second ODH catalyst to generate ethanol and acetaldehyde from the first-reactor effluent at an operating temperature of less than 450° C. and discharge a second-reactor effluent having ethylene, ethanol, acetaldehyde, and acetic acid as coproducts. The second-reactor effluent may include carbon dioxide, carbon monoxide, ethane, and water. The system may include a packed column to receive the second-reactor effluent. In some implementations, the packed column discharges an overhead stream having ethylene, ethane, carbon monoxide, and carbon dioxide, and discharges a bottoms stream having ethanol, acetaldehyde, acetic acid, and water.

In some embodiments, the ethylene produced using the systems and methods for coproduction in the production of ethylene described herein, or any of the processes or complexes described herein, can be used to make various olefin derivatives. Olefin derivatives include, but are not limited to, polyethylene, polypropylene, ethylene oxide, propylene oxide, polyethylene oxide, polypropylene oxide, vinyl acetate, vinyl chloride, acrylic esters (e.g., methyl methacrylate), thermoplastic elastomers, thermoplastic olefins, and blends and combinations thereof. The polyethylene can be produced using any suitable polymerization process and equipment. Suitable ethylene polymerization processes include, but are not limited to gas phase polyethylene processes, high pressure polyethylene processes, low pressure polyethylene processes, solution polyethylene processes, slurry polyethylene processes and suitable combinations of the above arranged either in parallel or in series. Further, the polyethylene can include homopolymers of ethylene or copolymers of ethylene and α-olefins, resulting in high density polyethylene (HDPE), medium density polyethylene (MDPE), low density polyethylene (LDPE), linear low density polyethylene (LLDPE), and very low density polyethylene (VLDPE).

EXAMPLES

This Example is given only as an example and not meant to limit the present techniques. In the Example, ethanol and acetaldehyde were synthesized over ODH catalyst from feed resembling a first-reactor effluent (e.g., 118 discussed above) from a first ODH reactor (e.g., 104). A laboratory ODH reactor simulating an implementation of the second ODH reactor 106 received the feed and was utilized for the synthesis that produced ethanol and acetaldehyde.

For simplification, CO and acetic acid were not included in the feed. The liquid in the feed was water, as noted in Table 1 below. The gas in the feed was ethane, ethylene, $O_2$, and $CO_2$, as given in Table 2 below.

Table 1 gives the liquid product from the synthesis in the laboratory ODH reactor receiving the feed of water, ethane, ethylene, $O_2$, and $CO_2$ listed collectively in Tables 1 and 2. Table 2 gives the gas product from the synthesis in the laboratory ODH reactor. Again, the laboratory ODH reactor acted as a second ODH in a series of two ODH reactors.

Figure 3:
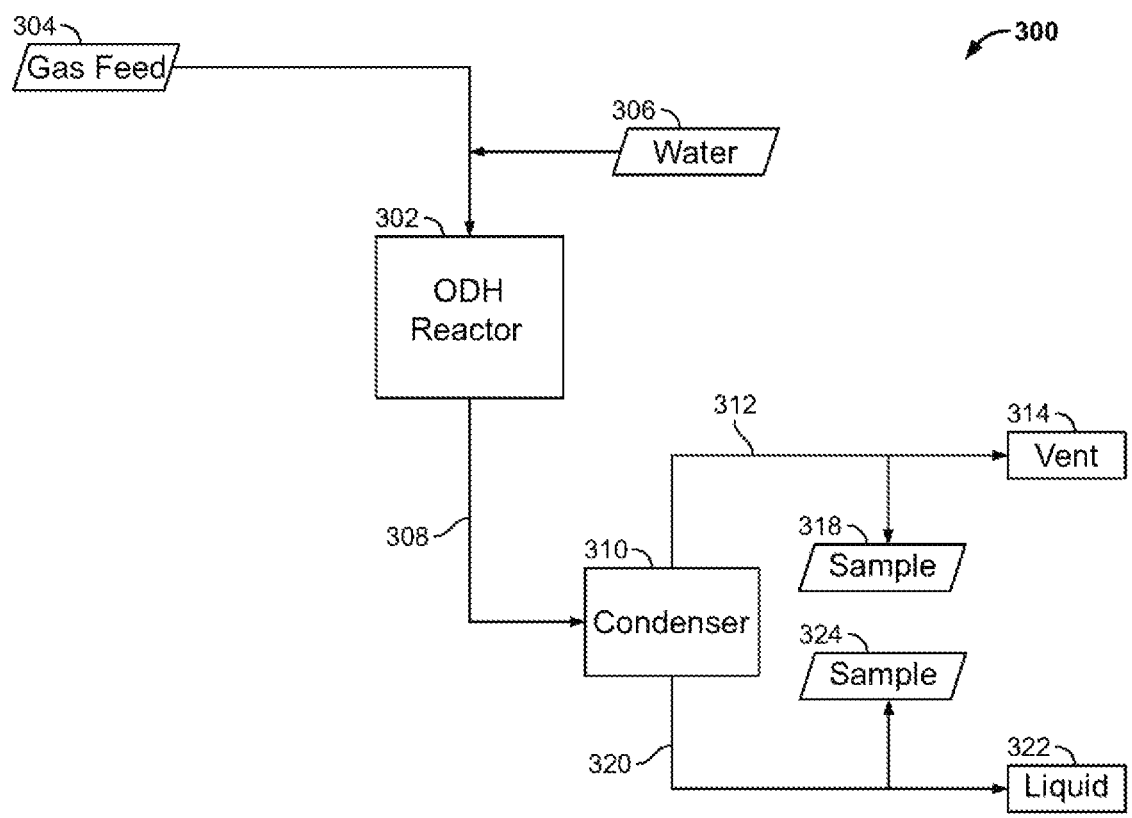
FIG. 3 is a block diagram of an ODH reactor system utilized to perform an Example.

FIG. 3 is the ODH reactor system 300 having the ODH reactor 302 employed to perform the Example synthesis over ODH catalyst that produced the ethanol and acetaldehyde from the feed resembling a first-reactor effluent from a first ODH reactor. The ODH reactor 302 is a large-scale laboratory reactor that is a continuous tubular fixed-bed reactor. As indicated, the ODH reactor 302 simulated a second ODH reactor of two ODH reactors disposed in series. The ODH reactor 302 may be characterized as an implementation of the second ODH reactor 106 previously described.

The ODH reactor 302 is a tubular fixed-bed reactor having two tubes disposed in series and with each tube having a fixed bed of catalyst. The two tubes are constructed of Type 316L stainless steel. The two tubes can each be characterized as two respective tubular fixed-bed reactors but the two tubes were operated collectively in the Example as a single tubular fixed-bed reactor.

The two tubes each have a heat transfer jacket that receives circulating oil from a closed-loop oil bath for heating or cooling of the two tubes to maintain a desired temperature in the reactor. In the Example, the reactor temperature was maintained in the range of 309° C. to 312° C. The temperature of the two tubes was monitored with thermocouples as temperature sensors.

The ODH catalyst in the two fixed beds is $Mo_{1.0}V_{0.37}Te_{0.23}Nb_{0.14}O_{d=4.97}$ with the numerical subscripts indicating molar ratios of the molybdenum, vanadium, tellurium, niobium, and oxygen, as determined by inductively coupled plasma mass spectrometry (ICP-MS). The ODH catalyst is available from NOVA Chemicals Corporation having headquarters in Calgary, Canada. The inside diameter of each tube is 2.1 centimeters (cm) giving a catalyst-bed diameter of 2.1 cm. The catalyst-bed height in the first tube is 128.5 cm. The catalyst bed height in the second tube is 135 cm. The two catalyst beds are diluted with a diluent powder. The mass ratio of diluent powder to catalyst is 1.22. The diluent powder is Versal™ Alumina V-250 manufactured by Honeywell UOP having headquarters in Des Plaines, Ill., United States of America. The mass of catalyst in the two beds combined is 171 grams. The mass of the diluent in the two beds combined is 209 grams. In preparation for addition to the reactor beds, the catalyst and diluent powder (alumina) are mixed together as powders and then extruded together into a cylindrical shape. The cylindrical extrudate shape has a diameter of about 1.7 millimeter (mm) and a length in the range of 2 mm to 10 mm.

A combined gas feed 304 of ethane, ethylene, and $CO_2$ was fed to the inlet of the ODH reactor 302 from respective gas cylinders of ethane, ethylene, and $CO_2$. The available pressure of the gas cylinders provided motive force for flow of the combined gas feed 304 into the ODH reactor 302. A respective flow valve associated with each gas cylinder gave the desired flow rate of each gas component. Water 306 as the liquid feed was introduced into the gas feed 304 flowing to the reactor 302. A pump provided the motive force for flow of the water 306 into the reactor 302.

The inlet pressure at the reactor 302 was 19 psig due to the hydraulic backpressure generated by flow of the feed gas through the reactor beds, downstream condenser, and associated piping. The linear velocity of the feed through the reactor 302 was 132 $cm^3$/sec. The GHSV was 717 $hour^{-1}$ ($h^{-1}$). The GHSV is the ratio of the volumetric flow rate of the gas feed 304 plus vapor feed generated from evaporation of liquid feed 306 at the inlet of reactor at standard conditions for temperature (25° C.) and pressure (100 kilopascals) to the combined volume of the two fixed-beds of catalyst. The weight hourly space velocity (WHSV) was 0.7 $h^{-1}$. The WHSV is the ratio of the weight (mass) flow rate of the total feed (gas feed 304 plus water 306) to the combined weight (mass) of the two fixed-beds of catalyst. The diluent powder is not counted (included) in the basis for the volume or weight of the catalyst bed. The weight and volume of the ODH active phase catalyst (mixed metal oxide) is the basis in the GHSV and WHSV calculations.

The product effluent 308 discharged from the reactor 302 to a condenser 310. The cooling medium in the condenser 310 was distilled water. The condenser 310 is a shell-and-tube heat exchanger with product gas on the tube side and the distilled water on the shell side. A product gas stream 312 discharged from the condenser 310 to a vent system 314. A sample syringe was utilized to collect a gas sample 318 of the product gas stream at a sample point downstream of the condensor 310. A liquid product stream 320 discharged from the condenser 310 to a liquid collection system 322. A liquid sample 324 of the liquid product stream 320 was obtained.

Tables 1 and 2 give the feed to the ODH reactor 302 as an implementation of the second reactor 106 (see FIG. 1). Again, the ODH reactor 302 acted as a second ODH in a series of two ODH reactors. Table 1 gives the liquid feed (water 306). Table 2 gives the gas feed (gas 304). The total feed is the combination of the liquid feed (Table 1) and the gas feed (Table 2). The total feed is a first-reactor effluent-type feed without CO and acetic acid. Table 1 gives the liquid product from the synthesis in the ODH reactor 302 receiving the total feed given collectively in Tables 1 and 2. Table 2 gives the gas product from the synthesis in the ODH reactor 302.

TABLE 1

Liquid Feed Composition and Liquid Product Composition

|  | Acetaldehyde wt % | Ethanol wt % | Acetic Acid wt % | Maleic Acid/ Anhydride wt % | H2O wt % |
|---|---|---|---|---|---|
| Liquid Feed (water 306) | 0.00 | 0.00 | 0.00 | 0.00 | 100.00 |
| Liquid Product (sample 324) | 0.18 | 0.12 | 0.68 | 0.03 | 98.99 |

TABLE 2

Dry Gas Feed Composition and Gas Product Composition

|  | C2H6 mol % | C2H4 mol % | O2 mol % | CO2 mol % | CO mol % |
|---|---|---|---|---|---|
| Gas Feed[1] (gas 304) | 11.48 | 80.08 | 0.00 | 8.43 | 0.00 |
| Gas Product (sample 318) | 12.98 | 79.23 | 0.00 | 7.78 | 0.01 |

[1]The wet feed gas composition (mol %) was C2H6/C2H4/CO2/H2O = 10.0/69.3/7.3/13.4

As can be seen in Tables 1 and 2, the product (effluent) from the ODH reactor 302 acting as a second reactor included acetaldehyde, ethanol, acetic acid, and ethylene. In implementations, the amount of coproducts, such as acetaldehyde and ethanol, produced may be increased by recirculating a portion of the product effluent back through the reactor.

A number of implementations have been described. Nevertheless, it will be understood that various modifications may be made without departing from the spirit and scope of the disclosure.

INDUSTRIAL APPLICABILITY

Coproduction of ethanol and acetaldehyde in oxidative dehydrogenation systems and methods.

The invention claimed is:

1. A method, comprising:
contacting ethane with a first oxidative dehydrogenation (ODH) catalyst in presence of oxygen in a first reactor to produce a first-reactor effluent comprising ethylene, carbon dioxide, and water;
removing oxygen from the first-reactor effluent upstream of a second reactor to provide a modified first-reactor effluent;
passing the modified first-reactor effluent from the first reactor to the second reactor; and
contacting the modified first-reactor effluent with a second ODH catalyst in the second reactor to form a second-reactor effluent comprising ethylene, ethanol, and acetaldehyde.

2. The method of claim 1, further comprising:
maintaining an operating temperature of the first reactor at less than 450° C.; and
maintaining an operating temperature of the second reactor at less than 450° C.,
wherein the second-reactor effluent further comprises carbon dioxide, carbon monoxide, and water.

3. The method of claim 1, wherein:
contacting the first-reactor effluent with the second ODH catalyst in the second reactor further forms acetic acid.

4. The method of claim 1, further comprising adding carbon dioxide to the second reactor to favor production of acetaldehyde over production of ethanol.

5. The method of claim 1, further comprising separating the second-reactor effluent into a liquid stream and a gas stream, wherein the liquid stream comprises the ethanol, the acetaldehyde, acetic acid, and the water, and the gas stream comprises the ethylene, ethane, the carbon dioxide, and carbon monoxide.

6. The method of claim 5, further comprising:
using a packed column to separate the second-reactor effluent into the gas stream and the liquid stream in a packed column;
discharging the gas stream overhead from the packed column; and
discharging the liquid stream from a bottom portion of the packed column.

7. The method of claim 6, further comprising diverting a portion of the modified first-reactor effluent to the packed column instead of to the second reactor, wherein:
the first ODH catalyst in the first reactor and the second ODH catalyst in the second reactor each comprise a mixed metal oxide having formula $Mo_aV_bTe_cNb_dPd_eO_f$;
a, b, c, d, e, and f subscripts are relative atomic amounts of elements Mo, V, Te, Nb, Pd, O, respectively; and
when a=1, b=0.01 to 1.0, c=0.01 to 1.0, d=0.01 to 1.0, 0.00≤e≤0.10, and f is a number to satisfy at least the valence state of the corresponding elements in the catalyst.

8. The method of claim 1, wherein:
the first reactor comprises the first ODH catalyst in a fixed bed;
the second reactor comprises the second ODH catalyst in a second fixed bed;
contacting the modified first-reactor effluent with the second ODH catalyst in the second fixed-bed reactor produces acetic acid; and
the second-reactor effluent further comprises carbon monoxide.

9. The method of claim 1, wherein removing oxygen from the first-reactor effluent upstream of the second reactor comprises flowing the first reactor effluent through an oxygen-separation vessel comprising a selective oxidation catalyst to remove oxygen from the first reactor effluent to provide the modified first-reactor effluent.

10. The method of claim 1, wherein the first ODH catalyst is a first fluidized bed of catalyst and the second ODH catalyst is a second fluidized bed of catalyst.

11. The method of claim 1, wherein the first-reactor effluent further comprises carbon monoxide, acetic acid, and unreacted ethane.

12. The method of claim 11, further comprising:
maintaining an operating temperature of the first reactor at less than 450° C.; and
maintaining an operating temperature of the second reactor at less than 450° C.,
wherein the second-reactor effluent further comprises carbon dioxide, carbon monoxide, and water.

13. The method of claim 11, further comprising:
maintaining an operating temperature of the first reactor at less than 450° C.; and
maintaining an operating temperature of the second reactor at less than 450° C.,
wherein the second-reactor effluent further comprises carbon monoxide.

14. The method of claim 11, wherein:
contacting the first-reactor effluent with the second ODH catalyst in the second reactor further forms acetic acid.

15. The method of claim 11, further comprising adding carbon dioxide to the second reactor to favor production of acetaldehyde over production of ethanol.

16. The method of claim 11, further comprising separating the second-reactor effluent into a liquid stream and a gas stream, wherein the liquid stream comprises the ethanol, the acetaldehyde, acetic acid, and the water, and the gas stream comprises the ethylene, ethane, the carbon dioxide, and carbon monoxide.

17. The method of claim 16, further comprising:
using a packed column to separate the second-reactor effluent into the gas stream and the liquid stream in a packed column;
discharging the gas stream overhead from the packed column; and
discharging the liquid stream from a bottom portion of the packed column.

18. The method of claim 11, wherein removing oxygen from the first-reactor effluent upstream of the second reactor comprises flowing the first reactor effluent through an oxygen-separation vessel comprising a selective oxidation catalyst to remove oxygen from the first reactor effluent to provide the modified first-reactor effluent.

* * * * *

UNITED STATES PATENT AND TRADEMARK OFFICE
CERTIFICATE OF CORRECTION

PATENT NO. : 11,760,704 B2
APPLICATION NO. : 17/630000
DATED : September 19, 2023
INVENTOR(S) : Vasily Simanzhenkov and Shahin Goodarznia It is certified that error appears in the above-identified patent and that said Letters Patent is hereby corrected as shown below:

In the Specification

In Column 1, Line 8, please replace "0371" with -- § 371 --.

Signed and Sealed this
Twenty-eighth Day of November, 2023

Katherine Kelly Vidal
*Director of the United States Patent and Trademark Office*